(12) United States Patent
Laffay et al.

(10) Patent No.: US 12,364,647 B2
(45) Date of Patent: Jul. 22, 2025

(54) BAG FOR SOLID CONCENTRATE (71) Applicant: FRESENIUS MEDICAL CARE DEUTSCHLAND GMBH, Bad Homburg (DE)

(72) Inventors: Philippe Laffay, Sainte Foy les Lyon (FR); Francois Dumont D'Ayot, Lyons (FR); Catherine Raymond, Bessenay (FR)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 589 days.

(21) Appl. No.: 17/296,992

(22) PCT Filed: Nov. 26, 2019

(86) PCT No.: PCT/EP2019/082635
§ 371 (c)(1),
(2) Date: May 26, 2021

(87) PCT Pub. No.: WO2020/109334
PCT Pub. Date: Jun. 4, 2020

(65) Prior Publication Data
US 2022/0023146 A1 Jan. 27, 2022

(30) Foreign Application Priority Data
Nov. 30, 2018 (FR) .................................. 1872167

(51) Int. Cl.
A61J 1/10 (2006.01)
A61J 1/14 (2023.01)
A61M 1/16 (2006.01)

(52) U.S. Cl.
CPC ............... *A61J 1/10* (2013.01); *A61J 1/1475* (2013.01); *A61M 1/1666* (2014.02); *A61M 1/167* (2014.02); *A61M 2207/10* (2013.01)

(58) Field of Classification Search
CPC ........ A61J 1/10; A61J 1/1475; A61M 1/1666; A61M 1/167; A61M 2207/10
See application file for complete search history.

(56) References Cited

U.S. PATENT DOCUMENTS 4,240,481 A * 12/1980 Bayham .................... A61J 1/10
604/408
4,396,382 A 8/1983 Goldhaber
(Continued)

FOREIGN PATENT DOCUMENTS

CN 102946840 A 2/2013
CN 103764192 A 4/2014
(Continued)

OTHER PUBLICATIONS

International Search Report and Written Opinion issued in corresponding International Patent Application No. PCT/EP2019/082635 dated Feb. 3, 2020 (9 pages).
(Continued)

Primary Examiner — Rebecca E Eisenberg
Assistant Examiner — Matthew Wrubleski
(74) Attorney, Agent, or Firm — Kilyk & Bowersox, P.L.L.C.

(57) ABSTRACT

The invention relates to a bag (1) made of a flexible wall, which bag is fitted with an inlet fluid line for introducing dissolution water, and with an outlet fluid line (121, 122) for extracting a solution obtained. According to the invention, the inside of the bag has a lower edge (13) in the overall shape of a V, the point of the V being further away from the centre of the bag than the arms of the V, the outlet fluid line
(Continued)

opening into the bag as close as possible to the point of the V.

18 Claims, 4 Drawing Sheets

(56) References Cited

U.S. PATENT DOCUMENTS

| | | | |
|---|---|---|---|
| 4,561,110 | A | 12/1985 | Herbert |
| 5,326,473 | A | 7/1994 | Lascombes et al. |
| 5,377,838 | A | 1/1995 | Segre |
| 5,972,223 | A | 10/1999 | Jonsson et al. |
| 8,333,751 | B2 * | 12/2012 | Kobashi ................ A61J 1/1481 604/408 |
| 8,617,134 | B2 | 12/2013 | Brehm et al. |
| 2002/0120227 | A1 | 8/2002 | Childers et al. |
| 2006/0172954 | A1 | 8/2006 | Jensen et al. |
| 2011/0137280 | A1 | 6/2011 | Ramella et al. |
| 2012/0288572 | A1 | 11/2012 | Kugelmann et al. |
| 2012/0310150 | A1 | 12/2012 | Brandl et al. |
| 2013/0190681 | A1 | 7/2013 | Jansson et al. |
| 2013/0281964 | A1 | 10/2013 | Kugelmann et al. |
| 2016/0206802 | A1 | 7/2016 | Schroeder et al. |
| 2016/0339227 | A1 * | 11/2016 | Tsai ................ A61M 39/1011 |
| 2018/0008761 | A1 | 1/2018 | Schroeder et al. |
| 2018/0303711 | A1 | 10/2018 | Kloeffel et al. |

FOREIGN PATENT DOCUMENTS

| | | |
|---|---|---|
| CN | 104582750 A | 4/2015 |
| CO | 5280187 A1 | 5/2003 |
| DE | 4316938 A1 | 12/1993 |
| EP | 3705144 A1 | 9/2020 |
| JP | 2001029457 A | 2/2001 |
| JP | 2005131221 A | 5/2005 |
| JP | 4059933 B2 | 3/2008 |
| JP | 2018164523 A | 10/2018 |
| KR | 10-2020-0023599 A | 3/2020 |
| WO | 9906083 A1 | 2/1999 |
| WO | 2019006173 A1 | 1/2019 |

OTHER PUBLICATIONS

Office Action issued in corresponding Taiwan Patent Application No. 108142723 dated Aug. 2, 2023 (14 pages).

Office Action issued in corresponding Colombian Patent Application NC2021/0008226 dated Apr. 18, 2023 (6 pages).

Office Action issued in corresponding European Patent Application 19806280.4 dated Jul. 21, 2022.

Office Action issued in corresponding Korean Patent Application No. 10-2021-7019950 dated Dec. 6, 2024 (22 pages).

Office Action issued in corresponding Chinese Patent Application No. 201910449358.5 dated Nov. 21, 2024 (11 pages)(Translation only).

* cited by examiner

BAG FOR SOLID CONCENTRATE

This application is a National Stage Application of PCT/EP2019/082635, filed Nov. 26, 2019, which claims priority to French Patent Application No. 1872167, filed Nov. 30, 2018.

The invention relates to a bag made of a flexible wall, which bag is fitted with an inlet fluid line for introducing dissolution water, and with an outlet fluid line for extracting a solution obtained.

Such bags are commonly used in the manufacture of haemodialysis solutions, notably solutions based on solid concentrate, such as solid base concentrate.

A haemodialysis treatment requires 120 to 240 l of dialysis solution. For dialysis using bicarbonate, the dialysis solution is produced on-line extemporaneously from an acid concentrate and a base concentrate.

The acid concentrate is generally made up of various electrolytes, of an acid, and of glucose. Because of the presence of several components with different dissolution rates, the acid concentrate is normally supplied in the form of a liquid concentrate. If a solid acid concentrate is used, it has to be dissolved in its entirety before the treatment in order to guarantee the exact composition of the liquid concentrate. The container for the solid concentrate therefore has to have enough volume to dissolve the entire contents before the treatment begins.

This requirement for complete dissolution prior to treatment is not needed for the base concentrate. Indeed, the base concentrate is generally made up of a single component: sodium bicarbonate. The liquid concentrate is a saturated solution thereof which can be produced continuously throughout the duration of the treatment. The bag containing the solid concentrate is connected to the haemodialysis generator which introduces water into the bag in a quantity such that a saturated solution is obtained. When this condition is met, the supply of water and the extraction of the saturated solution take place simultaneously until the solid concentration has been dissolved in its entirety.

For logistical and cost reasons, it is necessary for the bag to be as small as possible and for the quantity of bicarbonate to be as small as possible, while at the same time ensuring that it is sufficient to perform the treatment with one single bag. This is because changing bag during treatment takes time and a great deal of man power.

The prior art discloses various bags that allow the bicarbonate to be dissolved as effectively as possible. For example, the connector for connecting the bag to the haemodialysis generator may be fixed in the top of the bag. The water then flows into the concentrate from the top, while an extraction tube extracts the concentrate from the bottom of the bag. In order to improve the dissolution of the salt at the end of the procedure, it is known practice to incline the lower edge of the bag in order to cause the rest of the salt to drop into one of the two corners of the bag. The inclined edge acts like a ramp which forces any bicarbonate not yet dissolved to accumulate in the bottom of the bag in a volume that is as small as possible. In addition, the extraction tube may be positioned reliably in this area.

Inclining the bottom of the bag is not, however, an optimal solution, because the undissolved salt does not fall repeatably into the narrowed part of the bag. The inclination is of necessity fairly small if the size of the bag is not to be increased excessively. Studies have shown that the quantities of undissolved salt remaining in the bag fluctuate very widely. In order for the quantity required for a full treatment to be available in all instances it is necessary to provide a significant excess of bicarbonate, representing of the order of 100 to 200 g.

It is therefore an objective of the invention to modify the bags of the prior art in order to appreciably reduce the quantity of solid concentrate added in excess in order to guarantee a sufficient quantity of liquid concentrate for a haemodialysis, without by so doing appreciably increasing the size of the bag.

This objective is achieved through the fact that the inside of the bag has a lower edge in the overall shape of a V, the point of the V being further away from the centre of the bag than the arms of the V, the outlet fluid line opening into the bag as close as possible to the point of the V. By choosing two inclined edges (the two arms of the V) rather than just one, it is possible, while keeping a bag of normal size, to have the lower edge inclined sufficiently to ensure that the remains of solid concentrate drop under the effect of gravity into the point of the V which constitutes the lowermost point of the bag.

It is preferable for the joining area between the two arms of the V to be rounded. This avoids there being a corner in which salt accumulates and through which the dissolution water does not pass.

The two arms of the V may have the same inclination and/or the joining area between the two arms of the V may be located at the centre of the lower edge. The combination of these two features makes it possible to obtain a bag that is symmetrical. The arms of the V are preferably obtained by welding the bag onto itself.

In order to support the deformation of the bag when it is full and to avoid the formation of creases and the accompanying mechanical stresses, the lower edge of the bag may extend after each arm of the V, on the opposite side to the point of the V, by an intermediate area made up
- of a rounded shoulder, of which the gradient at the junction with the arms of the V is less than the gradient of the arms of the V and of which the gradient at its opposite end is close to vertical, and/or
- of a constriction nose projecting towards the centre of the bag to form an elbow, which constriction nose has the function of slightly reducing the cross section of the bag.

This intermediate area, particularly the rounded shoulder, avoids the formation of vertical creases in the V-shaped part.

In one preferred embodiment of the invention, the bag is made of two panels joined together via their outer edges, notably by welding the edges.

In one simple embodiment, the inside of the bag of the invention has an upper edge, a V-shaped lower edge, and two lateral edges each one connecting one end of the lower edge to the corresponding end of the upper edge, if appropriate with the interposition of an intermediate area between the V-shaped lower edge and the lateral edges. The bag preferably has a rectangular overall shape, the point of the V being located in the middle of one of the short sides of the rectangle, the bag extending beyond the V-shaped lower edge, on each side of the V, to an external lower edge parallel to the upper edge, the external lower edge preferably being at least partially coincident with the lower edge at the point of the V. It is thus possible to produce the bag according to the invention by superposing two rectangular panels of a suitable plastic sheet and by joining the two panels together by welding, bonding or any other suitable means, along the lateral edges, the upper edge, the V-shaped lower edge and, where appropriate, the external lower edge, the fixing-together (by welding, bonding, etc.) of the lateral edges preferably extending to the external lower edge.

The inlet fluid line preferably opens into the bag opposite the point of the V, thereby ensuring that the dissolution water passes through all of the solid concentrate contained in the bag before leaving the bag via the outlet fluid line which itself opens as close as possible to the point of the V.

The outlet fluid line may comprise a tube a first end of which is fitted with a filter, the tube being dimensioned to allow the filter to be positioned as close as possible to the point of the V. This filter allows the solution to be drawn off without carrying solid particles with it.

The bag may be fitted with a connector for connecting it to a haemodialysis generator, the connector being crossed by the inlet fluid line and a first portion of the outlet fluid line which is extended by a tube fitted at its opposite end with a filter positioned as close as possible to the point of the V, the first portion preferably being located opposite the point of the V. The connector can be inserted into an edge of the bag some distance away from the lower edge, preferably into an upper edge opposite the V-shaped lower edge. Another solution is to insert the connector into the wall of the bag some distance away from the V-shaped lower edge, preferably in its upper part.

The bag of the invention is particularly well suited to haemodialysis (HD) and haemodiafiltration (HDF). It may contain bicarbonate for the production of a saturated solution for dialysis.

The invention is described in greater detail with the aid of the following figures which show:

FIG. 1: a schematic view of a bag at the end of a dissolution procedure (a) according to the prior art, and (b) according to the invention;

FIG. 2: a view of the lower part of an empty bag (a) of the prior art and (b) of the invention;

FIG. 3: a view (a) from the front and (b) from the side of a filled bag of the invention.

For the sake of clarity, the description employs spatial references such as "lower" or "upper", "top" or "bottom", "vertical" or "horizontal". These references relate to a bag like those depicted in FIGS. 1a and 1b, with the connector positioned at the top.

The bag of the invention (1), like the bags of the prior art (9), is made up of two rectangular panels of a flexible sheet of plastic. For an application in the field of dialysis, the bag can be made of low density polyethylene (PELD), from a mixture of polyamide and low density polyethylene (PA/PELD) or of low density polyethylene and high density polyethylene (PELD/PEHD) or even of a two-layer material. The two panels are fixed together via their exterior edges, so that the empty bag is flat at least in its lower part. Fixing is performed preferably by welding, although other methods of fixing such as bonding may be envisaged. For the sake of clarity, only the terms "welded" or "welding" will be used in the remainder of the procedure, although these are not limiting features, it being possible for any other method of fixing compatible with the use for which the bag is intended, notably bonding, to be applied to the invention. In the example given here, the bags have two lateral edges (11b, 11d, 91b, 91d), a lower external edge (11c, 91c) and an upper edge (11a, 91a). The lateral edges, the external lower edge and the upper edge are substantially straight when the bag is empty. Rather than two panels which are superposed and welded via their exterior edges, it would also be possible to use a tubular wall closed at its two ends, for example by welding, or else a sheet folded in two and closed along its superposed edges, notably by welding. The overall shape of the bag, rectangular in this instance, and the number of edges has no importance. It would be possible to envisage bags of trapezoidal, triangular or even circular overall shape.

Extraction means (12, 92) are positioned in one of the edges of the bag (11a, 91a) or in the wall of the bag some distance away from the edges. In general, these extraction means comprise two fluid lines, one for introducing water for dissolving the sodium bicarbonate and the other for extracting the solution obtained contained in the bag. In the examples given here, the extraction means consist of a connector (12, 92) of the kind of that disclosed in patent application EP 1 344 550 A1. It has the advantage of combining extraction means and means of connection to a haemodialysis generator. The connector (12, 92) is inserted into the upper edge (11a, 91a). It might very well be possible to provide any other type of extraction means without these necessarily performing the additional function of acting as connection means. Two distinct nozzles inserted into the upper edge (11a, 91a) such as those disclosed in U.S. Pat. No. 4,561,110 may be mentioned by way of another possible embodiment example. The nozzles could be inserted into two distinct edges, notably two opposite edges. It might also be possible to provide a single fluid line used for introducing the solubilisation water and for extracting the finished solution.

The two fluid lines of the connector (12, 92) open into the top of the bag (1, 9). The outlet fluid line of the connector (12, 92) is fitted with a flexible tube (121, 921) ending in a filter (122, 922). The length of the flexible tube is chosen so that the filter is positioned in the bottom part of the bag. The dissolution water is thus introduced into the top of the bag, passes through the solid concentrate getting saturated and the saturated solution is withdrawn from the bottom part passing through the filter and the flexible tube.

In order for the solid concentrate to accumulate at the end of the procedure in a space that is as small as possible, the cross section of the bottom part of the bag narrows. In bags of the prior art (9), this narrowing is obtained by creating an inclined weld (93) positioned between one of the two corners (91e) of the bottom part of the bag and the opposite lateral edge (91d). The inclined weld has two sections with different gradients: the first (931), near the bottom corner (91e) is not as steeply inclined as the second (932) near the lateral edge (91d) opposite the corner (91e). In the example given here, the first section is inclined with respect to the horizontal (or to the external lower edge 91c) by around 20°, the second by around 38°. The 20° gradient makes it possible to follow the radius of curvature of the tube and get the end of the filter into the corner of the bag, whereas the 38° gradient allows the powder to drop down as it gradually dissolves. The filter (922) fixed to the end of the flexible tube rests on the first section with its end as close as possible to the lowermost point (94). The second section is a compromise. Specifically, the steeper the gradient, the more easily the concentrate slides down along the inclined weld, but also the greater volume of bag (933) is lost between this inclined weld and the second corner (91f) of the bottom part of the bag. Now, to compensate for the lost volume while maintaining the same working volume, it is necessary to increase the height of the bag.

Furthermore, when the bag of the prior art is full of solid concentrate, and also throughout the dissolution procedure, it has a tendency to deform asymmetrically so that a kind of crease appears in the wall of the bag. In order to ensure that the filter does indeed rest on the first section (931) of the inclined weld with its end at the lowermost point (94) of the bag, the tube (921) needs to be fixed to the fluid line of the connector (92) opposite the corner (91e) at which the lowermost point is located, otherwise there is a risk that the filter might not rest at the lowermost point of the bag when the bag has deformed.

The more the dissolution progresses, the less solid concentrate there is in the bag. Under the effect of gravity, the solid concentrate has a tendency to accumulate in the bottom part of the bag. However, experience has shown that, at the end of the procedure, a proportion of solid concentrate remains caught on the walls of the bag at the inclined weld (93) as indicated schematically in FIG. 1a. A kind of furrow forms in the accumulated solid which means that the dissolution water no longer passes through the solid concentrate. Studies conducted with haemodialysis bags have shown that between 2.1% and 21.6% of solid concentrate (bicarbonate) can remain at the end of the procedure, these values varying according to the initial volume of solid concentrate and according to the dissolution rate. This furrow effect is notably caused by the fact that the dissolution water is introduced substantially in alignment with the filter, therefore playing no part in carrying the solid concentrate towards the lowermost point where the filter is located. The presence of the tube (921) along part of the inclined weld also encourages solid retention. In order to compensate for this fraction of retained product, it is therefore necessary to provide more solid concentrate than is theoretically necessary. The wide range (2.1% to 21.6%) observed shows how the quantity withdrawn greatly lacks repeatability. It is therefore necessary for the excess product to be sufficient in quantity to make it possible in all instances to obtain the nominal volume of solution. In practice, the excess is comprised between 100 and 200 g according to the size of the bag.

The bag of the invention has been developed to significantly decrease the excess product that needs to be added to the bag in order to guarantee the nominal volume of solution. The lower edge of the bag of the invention (1) for its part has a V shape, the point of the V being opposite the upper edge (11a) and constituting the lowermost point (14) of the bag. The two edges (13) that form the arms of the V are made up of two inclined welds (13) extending between approximately the middle of the external lower edge (11c) and one of the lateral edges (11b, 11d). At the junction between the two arms of the V, the two inclined welds (13) are separated by a rounded joining area (132), notably in the shape of an arc of a circle. This joining area constitutes the lowermost point (14) of the bag. By moving this lowermost point (14, 94) from a corner of the bag (91e) to the centre of the lower edge (11c) and by choosing two inclined welds (13) rather than one (93), it is possible to choose far steeper inclinations while at the same time having relatively small lost volumes (131) between the inclined welds (13) and the corresponding lower corners (11e, 11f). It would of course be possible to cut away the material that forms the lost volumes (131) but this additional step is not necessary per se. It is simpler to use two rectangular panels and weld not only the edges (11a, 11b, 13, 132, 13, 11d) that form the actual bag proper, but also the external lower edge (11c) and the continuation of the lateral edges as far as the external lower edge (11c) forming the lower corners (11e, 11f). That stops the panels in the lost volumes (131) from being free. In addition, welding the corners stiffens these parts so that they do not have a needless tendency to bend. It may be seen from FIG. 2b that the external lower edge (11c) and the bottom of the joining area (132), that forms the point of the V and the lowermost point of the bag, are coincident.

Figure 1A:
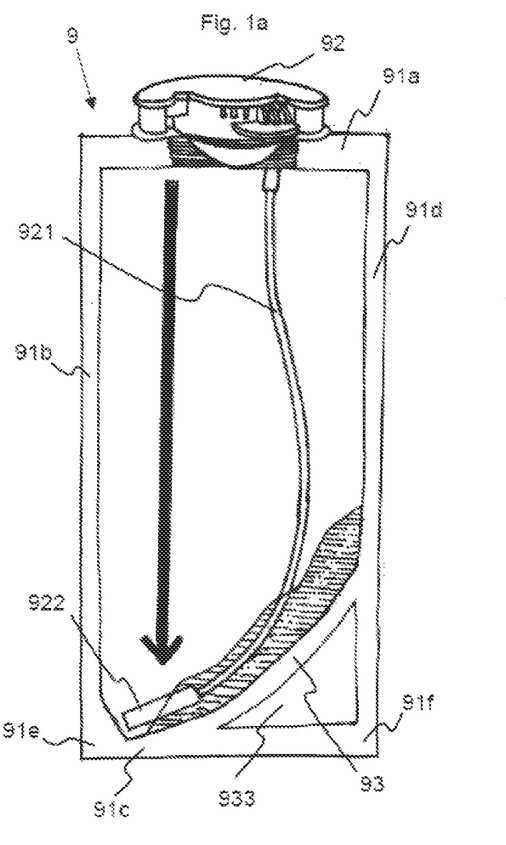

Furthermore, because the bag is symmetrical, there is no asymmetric deformation as there is with the bag of the prior art (cf. FIG. 1a). The length of the tube (121) can be chosen so that only the filter rests on the wall of the bag at one of the inclined welds (13). The tube (121) therefore does not trap solid along the weld as it did in the bag of the prior art.

The angle (α) between the two arms of the V (13) is preferably comprised between 65° and 75°.

In order to support the deformation of the bag when it is full and to avoid the formation of creases and the accompanying stress areas, an intermediate area (15) may be provided between the top of the arms of the V (13) and the lateral edges (11b, 11d). In the example given in FIGS. 1b and 2b, this intermediate area consists of a concave shoulder (151), preferably in the shape of an arc of a circle, and of a constriction nose (152). The gradient of the shoulder at the junction with the top of the inclined weld (13) is not as steep as the gradient of the inclined weld. The gradient of the shoulder increases evenly until it becomes substantially vertical. At this point, the width of the edge of the bag is at least equal to the overall width of the lateral edge (11b, 11d) outside of this intermediate area. The shoulder (151) then gives over to the constriction nose (152) which, in a lower part, assumes and continues the concave shape, diverging towards the centre of the bag as far as an elbow (152'). From the elbow, the edge of the bag diverges again from the centre of the bag. The length of the edge between the junction with the shoulder (151) and the elbow is preferably shorter than the length between the elbow and the junction with the lateral edge (11b, 11d) or, in other words, the first part is more steeply inclined (with respect to the vertical) than the second. If the outline of the empty bag is rectangular, the width of the edge of the bag in this constriction nose (152) increases therefore as far as the elbow before decreasing again, but more gently, until it returns to the width of the lateral edge (11b, 11d). The shoulder (151) and the start of the constriction nose (152) together form a kind of cavity (153). The constriction nose need not extend as far as the upper edge (11b). It is enough for it to begin a few centimetres away from the top of the arms of the V. When the bag is full of dry sodium bicarbonate, but especially with the salt and with the dissolution water, the bag swells by around 3 to 4 cm, exerting tension on the welded edges. The presence of the cavity (153) and of the narrowing snout (152) contributes to better distribution of the pressure and stresses over the welded edges. The rounded shape of the cavity (153) also makes it possible to reduce the risks of leakage, such as are encountered with angular parts.

Figure 4:
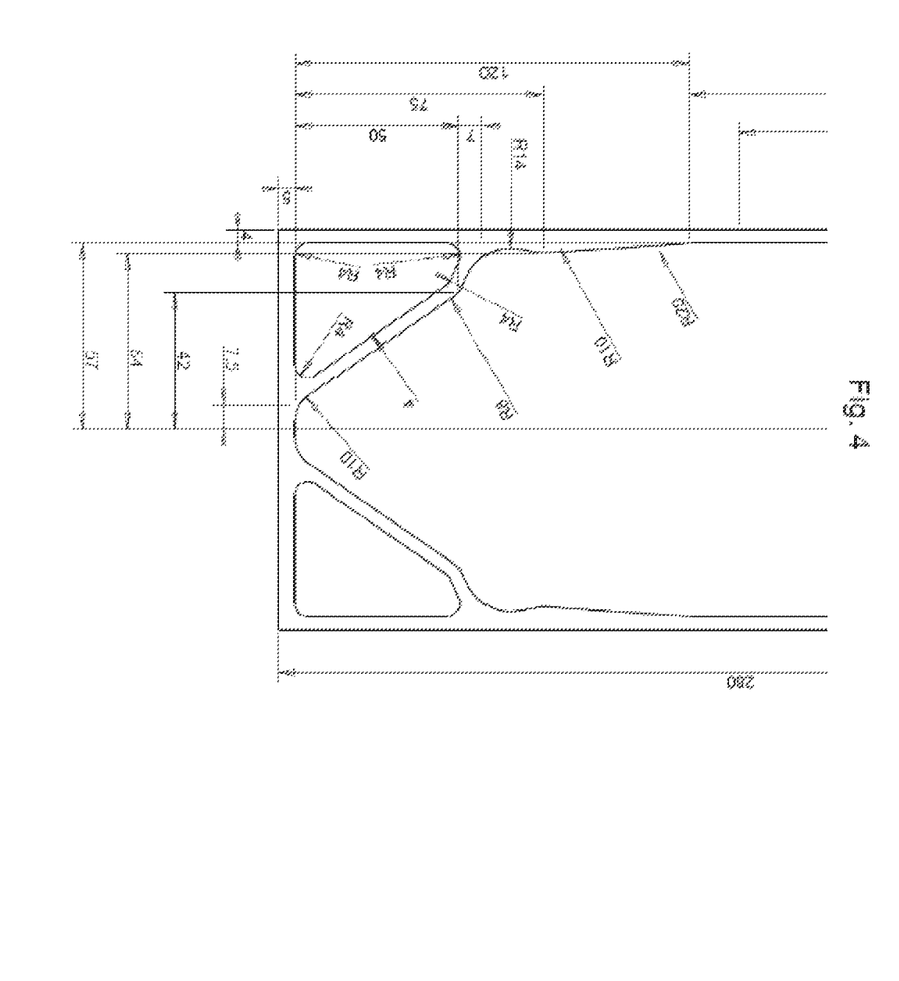
FIG. 4: one specific exemplary embodiment of the bag of the invention.

By way of nonlimiting example depicted in detail in FIG. 4, for a bag 280 mm high and 122 mm wide, the overall width of the welded edges (11a-d, 13, 132, 151) is around 4 mm (a little more in the area of the elbow of the constriction nose), the rounded joining area that forms the point of the V has a width of around 15 mm, the inclination of the welded edges (13) with respect to the horizontal (or with respect to the external lower edge 11c) is around 55°, namely an angle (a) of 70° between the arms of the V (13). In the remainder of the description of the example, reference is made to the 0 mm measurement which corresponds to the bottom of the joining area, namely the lowermost point of the bag (14). The inclined weld extends between the end of the joining area, 7.5 mm away from the centre of the lower edge (11b), and the 50 mm measurement, 42 mm away from the centre of the lower edge (11b). Between the 50 mm and 120 mm measurements, the inclined weld (13) gives way to a weld that forms the intermediate area (15) between the inclined weld (13) and the weld of the lateral edge (11b, 11d). This intermediate area begins at the rounded shoulder (151) which extends as far as the 64 mm measurement, 56 mm away from the centre of the lower edge. It is continued by the constriction nose (152) in which the width of the edge of bag increases as far as the elbow (152') at the 75 mm measurement, 54 mm away from the centre of the lower edge, before decreasing continuously again as far as the 120 mm measurement, where the thickness is the same as in the rest of the lateral edge, namely around 4 mm. The radius of curvature of the cavity (153) is 14 mm.

The welds that form the bottom part of the bag (11b, 152, 151, 13, 132, 13, 151, 152, 11d) are produced in such a way that inside the bag they describe a continuous path without corners liable to trap solid product, liable to disturb the flow of the liquid and/or liable to cause the bag to deform.

Figure 1B:
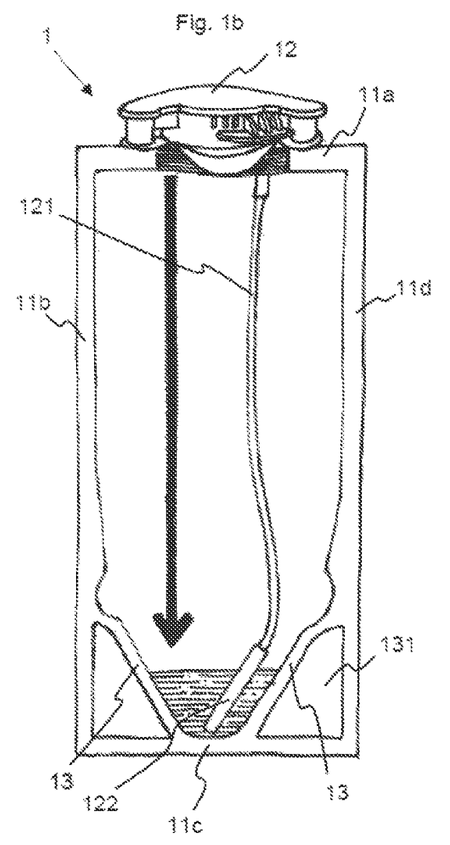
Figure 2A:
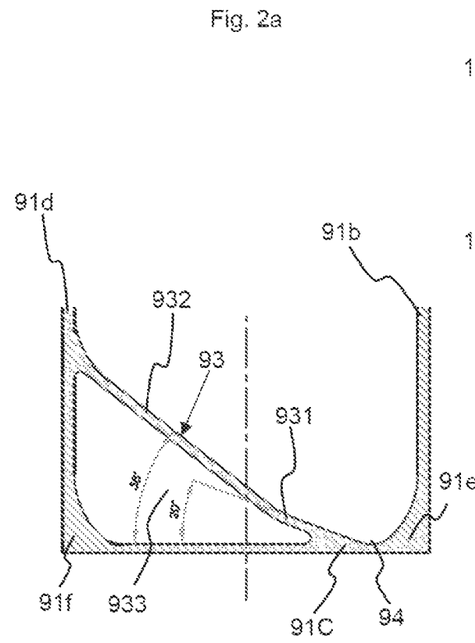
Figure 2B:
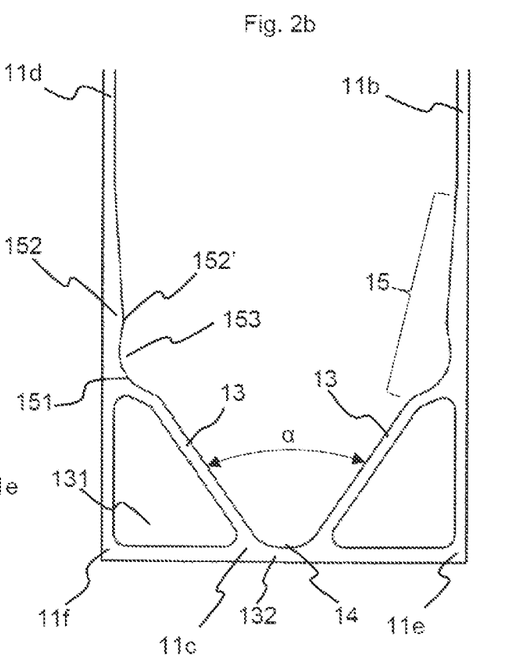
Figure 3A:
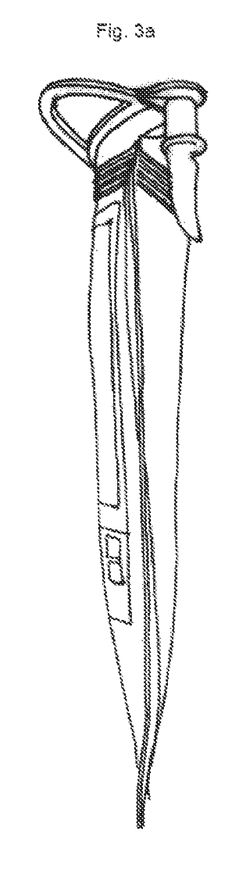
Figure 3B:
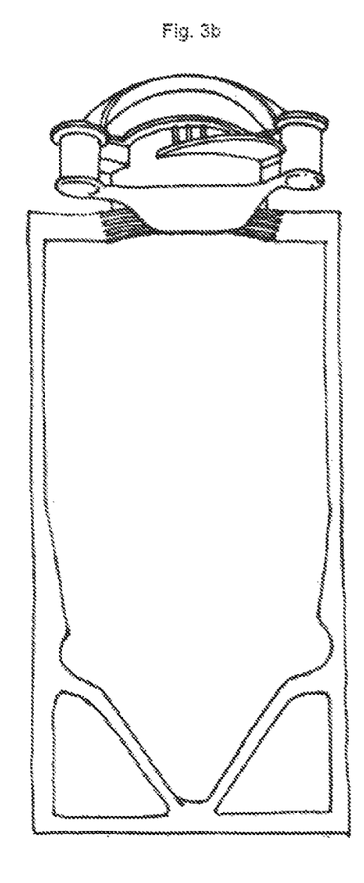

In the example given in FIGS. 1b and 2b, the point of the V (132) is located at the centre of the external lower edge (11c) of the bag (1) and therefore in the middle of the V-shaped edge (13, 132). The bag is symmetrical which means that there is no need to orientate the connector (12) in order for the filter (122) to lie at a particular point, as was needed with the bag of the prior art. In some instances, however, it might be possible to move the point of the V away from the centre of the external lower edge (11c) but without moving it as far as one of the corners (11e, 11f).

Studies performed with bags according to the invention, full of bicarbonate for haemodialysis have shown that only 1.2% and 5.2% of the solid product remained undissolved at the end of the procedure. Thanks to the bag of the invention (1) with its inclined welds (13) steeply angled with respect to the horizontal (55° in the example given, as opposed to 38° in the bag of the prior art), it is possible to considerably reduce the excess of product to be provided in the bag in order to guarantee the nominal volume of solution. In the example of bags intended for haemodialysis, the saving is 50 g of bicarbonate for 500 and 600 g bags, and 100 g for 900 g bags. This represents a 50% reduction in wastage. Not only because of the geometry adopted but also because of the smaller quantity of bicarbonate contained in the bag, it is possible to reduce the size of the bags, and notably to reduce their height. In the case given here, the height of the bag of the invention is 4 cm less than the bag of the prior art for the same width. This makes it possible to save not only on bag material but also on storage space for the empty bags before they are filled and for the bags which are ready for use.

LIST OF REFERENCES

1 Bag of the invention
   11a-d Lateral edges of the bag
   11e-f Lower corners
   12 Extraction means
      121 Flexible tube
      122 Filter
   13 Inclined edges
      131 Lost volumes
      132 Joining area
   14 Lowermost point of the bag
   15 Intermediate area
      151 Shoulder
      152 Nose
      152' Elbow of the nose
      153 Cavity
   α Angle between the arms of the V
9 Bag of the prior art
   91a-d Lateral edges of the bag of the prior art
   91e $1^{st}$ bottom corner from which the inclined edge begins
   91f $2^{nd}$ bottom corner
   92 Extraction means
      921 Flexible tube
      922 Filter
   93 Inclined edge
      931 $1^{st}$ section of shallower gradient
      932 $2^{nd}$ section of steeper gradient
      933 Lost volume
   94 Lowermost point of the bag

The invention claimed is:

1. A bag made of a flexible wall, the bag having two opposing inner lateral edges, two opposing inner intermediate sections, a lower inner edge, and an upper inner edge, the bag being fitted with an inlet fluid line for introducing dissolution water, and with an outlet fluid line for extracting a solution obtained, wherein
the lower inner edge is in the overall shape of a V,
the V has a point, and two arms with each arm having a top,
the point of the V is further away from the center of the bag than the arms of the V,
the outlet fluid line opens into the bag as close as possible to the point of the V,
each arm extends from the point of the V, to a respective one of the opposing inner intermediate sections,
each inner intermediate section extends from the top of the respective arm to a respective one of the inner lateral edges and comprises a concave shoulder, a constriction nose, an elbow, and a cavity,
in an empty state of the bag, each concave shoulder starts at the top of the respective arm of the V and gives over to the respective constriction nose,
in an empty state of the bag, each constriction nose, in a lower part, assumes and continues the concave shape of the respective shoulder and diverges towards the center of the bag as far as the respective elbow,
each cavity has a rounded shape and extends from the top of the respective arm to the respective elbow, and
the inner width of the bag narrows between the opposing elbows such that the maximum inner width of the bag between the opposing cavities is greater than the inner width of the bag between the opposing elbows.

2. The bag according to claim 1, wherein the point of the V is rounded.

3. The bag according to claim 1, wherein, the two arms of the V have a same inclination and/or a joining area between the two arms of the V is located at a center of the lower inner edge.

4. The bag according to claim 1, wherein an angle (α) between the two arms of the V is between 65° and 75°.

5. The bag according to claim 1, wherein the arms of the V are obtained by welding the bag onto itself.

6. The bag according to claim 1, wherein each concave shoulder has a first gradient at a junction with the respective arm of the V, each concave shoulder has a second gradient as the concave shoulder approaches the respective elbow, each arm of the V has a respective gradient, the first gradient is less than the gradient of the respective arm, and the second gradient is steeper than the first gradient and close to vertical.

7. The bag according to claim 1, wherein the bag is made of two panels joined together via outer edges.

8. The bag according to claim 1, wherein the upper inner edge has a first end and a second end, and each inner lateral edge connects a respective one of the first end and the second end to a respective one of the inner intermediate sections.

9. The bag according to claim 8, wherein the bag has a rectangular overall shape that includes short sides and long sides, the point of the V is located in the middle of one of the short sides of the rectangle, the bag extends beyond the lower inner edge, on each side of the V, to an external lower edge that is parallel to the upper inner edge.

10. The bag according to claim 1, wherein the inlet fluid line opens into the bag opposite the point of the V.

11. The bag according to claim 1, wherein the outlet fluid line comprises a tube, a first end of the tube is fitted with a filter, and the tube is dimensioned to allow the filter to be positioned as close as possible to the point of the V.

12. The bag according to claim 1, wherein the bag is fitted with a connector for connecting the bag to a haemodialysis generator, the connector is crossed by the inlet fluid line and a first portion of the outlet fluid line, the first portion is extended by a tube connected to the first portion at a first end of the tube, and the tube is fitted at a second end of the tube, which is opposite the first end, with a filter positioned as close as possible to the point of the V.

13. The bag according to claim 12, wherein the connector is inserted into an edge of the bag at a distance spaced away from the lower inner edge.

14. The bag according to claim 1, wherein the bag contains bicarbonate for the production of a saturated solution for dialysis.

15. The bag according to claim 1, wherein the bag is made of two panels joined together via outer edges by welding.

16. The bag according to claim 8, wherein the bag has a rectangular overall shape that includes short sides and long sides, the long sides include respective external lateral edges, the point of the V is located in the middle of one of the short sides of the rectangle, the bag extends beyond the lower inner edge, on each side of the V, to an external lower edge that is parallel to the upper inner edge, the point of the V is formed by a weld seam having a weld seam external edge, the external lower edge is at least partially coincident with the weld seam external edge, and the external lateral edges extend to the external lower edge.

17. The bag according to claim 1, wherein the bag is fitted with a connector for connecting the bag to a haemodialysis generator, the connector is crossed by the inlet fluid line and a first portion of the outlet fluid line, the first portion is located opposite the point of the V, the first portion is extended by a tube connected to the first portion at a first end of the tube, and the tube is fitted at a second end of the tube, which is opposite the first end, with a filter positioned as close as possible to the point of the V.

18. The bag according to claim 12, wherein the connector is inserted into an external edge of the bag at a distance spaced away from the point of the V, inserted into an upper external edge of the bag opposite the point of the V, or inserted into the wall of the bag at a distance spaced away from the point of the V.

* * * * *